United States Patent
Pistrol et al.

(10) Patent No.: US 9,645,071 B2
(45) Date of Patent: May 9, 2017

(54) METHOD TO DETERMINE A SLIP STATE OF THE COMPACTOR ROLLER OF A SOIL COMPACTOR CAUSED BY AN OSCILLATION MOTION OF A SOIL COMPACTOR

(71) Applicant: Hamm AG, Tirschenreuth (DE)

(72) Inventors: Johannes Pistrol, Mödling (AT); Fritz Kopf, Vienna (AT); Werner Völkel, Neustadt (DE); Sebastian Villwock, Pechbrunn (DE)

(73) Assignee: HAMM AG, Tirschenreuth (DE)

( * ) Notice: Subject to any disclaimer, the term of this patent is extended or adjusted under 35 U.S.C. 154(b) by 127 days.

(21) Appl. No.: 14/631,415

(22) Filed: Feb. 25, 2015

(65) Prior Publication Data

US 2015/0241333 A1 Aug. 27, 2015

(30) Foreign Application Priority Data

Feb. 27, 2014 (DE) .................. 10 2014 203 585

(51) Int. Cl.
  *E01C 19/23* (2006.01)
  *G01N 19/02* (2006.01)
  *E01C 19/28* (2006.01)

(52) U.S. Cl.
  CPC ............. *G01N 19/02* (2013.01); *E01C 19/23* (2013.01); *E01C 19/288* (2013.01)

(58) Field of Classification Search
  CPC .......... E01C 19/23; E01C 19/28; E01C 19/22; E02D 3/026; E02D 3/02
  See application file for complete search history.

(56) References Cited

U.S. PATENT DOCUMENTS

| | | | | |
|---|---|---|---|---|
| 4,103,554 A | * | 8/1978 | Thurner | E02D 3/046 404/133.05 |
| 4,149,253 A | * | 4/1979 | Paar | E02D 3/026 404/117 |
| 4,212,071 A | * | 7/1980 | Dortu | E01C 19/23 175/19 |

(Continued)

FOREIGN PATENT DOCUMENTS

| | | |
|---|---|---|
| CN | 103161116 A | 6/2013 |
| DE | 3590610 C2 | 9/1997 |

(Continued)

OTHER PUBLICATIONS

German search report issued for German patent application No. DE 10 2014 203 585.6 dated Oct. 1, 2014, with machine English translation (13 pages).

(Continued)

*Primary Examiner* — David A Rogers
(74) *Attorney, Agent, or Firm* — Rothwell, Figg, Ernst & Manbeck, P.C.

(57) ABSTRACT

A method to determine a slip state of the compactor roller of a soil compactor caused by an oscillation motion of a compactor roller, comprising the steps:
  a) Preparation of an acceleration quantity related to the oscillation motion of the compactor roller
  b) Based on the acceleration quantity, preparation of an acceleration frequency spectrum,
  c) Based on the acceleration frequency spectrum, determining the slip state of the compactor roller.

7 Claims, 5 Drawing Sheets

(56) References Cited

U.S. PATENT DOCUMENTS

Figure 1:
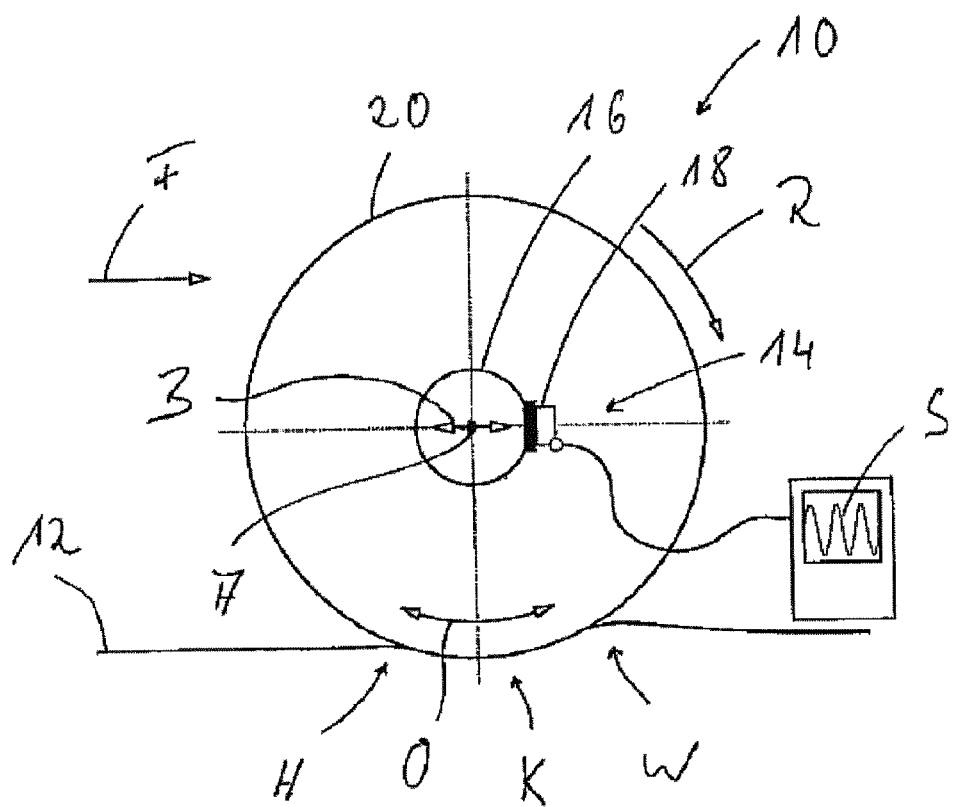

| | | | | |
|---|---|---|---|---|
| 4,348,901 | A * | 9/1982 | Vural | E02D 3/046 404/133.05 |
| 4,422,795 | A * | 12/1983 | Berrange | E02D 3/026 301/1 |
| 4,467,652 | A * | 8/1984 | Thurner AB | E02D 3/046 404/133.05 |
| 4,546,425 | A * | 10/1985 | Breitholtz | E01C 19/288 366/128 |
| 4,647,247 | A * | 3/1987 | Sandstrom | E01C 19/286 172/40 |
| 4,870,601 | A | 9/1989 | Sandstroem | |
| 5,164,641 | A * | 11/1992 | Quibel | E01C 19/288 318/128 |
| 5,177,415 | A * | 1/1993 | Quibel | E01C 19/288 318/128 |
| 5,695,298 | A * | 12/1997 | Sandstrom | E01C 19/286 404/117 |
| 5,719,338 | A * | 2/1998 | Magalski | E01C 19/288 404/117 |
| 5,727,900 | A * | 3/1998 | Sandstrom | G01P 15/18 404/122 |
| 5,924,509 | A * | 7/1999 | Ferguson | B60K 28/165 180/197 |
| 5,942,679 | A * | 8/1999 | Sandstrom | E01C 19/26 404/133.05 |
| 6,188,942 | B1 * | 2/2001 | Corcoran | E01C 19/006 701/408 |
| 6,382,873 | B1 * | 5/2002 | Mulders | E01C 19/235 172/148 |
| 6,558,072 | B2 * | 5/2003 | Staffenhagen | E01C 19/286 404/117 |
| 6,712,550 | B2 * | 3/2004 | Fervers | E02D 3/026 404/122 |
| 6,750,621 | B2 * | 6/2004 | Gandrud | E01C 19/288 318/114 |
| 6,752,567 | B2 * | 6/2004 | Miyamoto | E01C 19/288 404/117 |
| 7,089,823 | B2 * | 8/2006 | Potts | E01C 19/288 404/117 |
| 7,873,492 | B2 * | 1/2011 | Ackermann | E01C 19/288 702/150 |
| 9,039,319 | B2 * | 5/2015 | Oetken | E01C 19/288 404/75 |
| 9,222,226 | B2 * | 12/2015 | Villwock | E02D 3/026 |
| 2006/0096354 | A1 * | 5/2006 | Commuri | E01C 19/288 73/32 A |
| 2014/0341650 | A1 * | 11/2014 | Villwock | E02D 3/026 404/117 |

FOREIGN PATENT DOCUMENTS

| | | |
|---|---|---|
| JP | 2000-110111 A | 4/2000 |
| JP | 2000-345512 A | 12/2000 |
| JP | 2003-193416 A | 7/2003 |
| JP | 3552028 B2 | 8/2004 |
| JP | 3908031 B2 | 4/2007 |

OTHER PUBLICATIONS

Office Action issued for Japanese Patent Application No. 2015-032522 dated Jan. 8, 2016, along with machine English translation (6 pages).

Office Action issued for Chinese Patent Application No. 201510061280.1 dated Sep. 5, 2016 (7 pages).

* cited by examiner a)

b)

a)

b)

METHOD TO DETERMINE A SLIP STATE OF THE COMPACTOR ROLLER OF A SOIL COMPACTOR CAUSED BY AN OSCILLATION MOTION OF A SOIL COMPACTOR

CROSS REFERENCE TO RELATED APPLICATION(S)

This application claims priority to German Application No. 10 2014 203 585.6, filed Feb. 27, 2014. The entirety of the disclosure of the above-referenced application is incorporated herein by reference.

BACKGROUND OF THE INVENTION

Field of the Invention

The present invention relates to a method by means of which in the course of a compacting process performed by a soil compactor having at least one compactor roller, a quantity can be determined which represents the slip of such a compactor roller with respect to the subsoil being compacted.

Description of the Related Art

To perform compacting processes in soil construction engineering or in road building, for example, for asphalt compacting, in general soil compactors are used which have at least one compactor roller. With a compactor roller of this type, the soil compactor moves over the subsoil being compacted, and due to the static load of the compactor roller, the compacting process is implemented. In order to obtain more efficient compacting, the known prior art provides for superimposing periodic motions on the essentially uniform rotation motion of the compactor roller during the corresponding, essentially uniform forward movement of a soil compactor. During an oscillation motion superimposed on the rotational motion of the compactor roller, the compactor roller is excited by, for example, imbalance masses arranged in the interior thereof to perform a periodic back-and-forth rotation or forward-backward rotation. Due to the friction between a roller mantle of the compactor roller and the surface of the subsoil being compacted, shear forces are introduced into the subsoil. The shear distortions caused thereby lead to intensified compacting of the subsoil transited by one such compactor roller.

Document DE 35 90 610 C2 discloses a method by which the degree of compaction of the subsoil can be determined based on the horizontal acceleration of the compactor roller determined in the course of one such oscillation motion of a compactor roller, thus based on an acceleration essentially in the direction parallel to the surface of the compacted subsoil. It is taken into account here that in the course of one such periodic oscillation motion, phases occur in which the acceleration of the compactor roller is so great that a slip occurs between the surface of the roller mantle and the subsoil. In these phases the horizontal acceleration of the compactor roller remains essentially constant, whereas in phases in which the compactor roller exhibits essentially no slip with respect to the subsoil being compacted, the acceleration essentially follows the pattern of a periodic curve, such as a sine curve, for example. Based on the frequency of the oscillation motion itself, and the progression of horizontal acceleration during phases when the compactor roller displays no slip on the subsoil, in this known method a conclusion can be drawn about the degree of compaction of the subsoil to be compacted.

The slip occurring upon implementation of a compacting process by use of periodic oscillation motions of a compactor roller between the outer surface of the roller mantle and the subsoil being compacted increases with increasing degree of compaction, thus in general also with increasing hardness or stiffness of the subsoil to be compacted. Since this subsoil in general is constructed with abrasive material, that is, stone material or stone fractions, an excessively powerful slip between the compactor roller and the subsoil being compacted can result in excessive wear on the roller mantle of one such compactor roller.

SUMMARY OF THE INVENTION

The object of the present invention is to provide a method for determining the slip state of the compactor roller of a soil compactor caused by an oscillation motion of a compactor roller, so that in a simple and dependable manner a conclusion can be drawn about the slip of a compactor roller with respect to the soil being compacted, as occurs in the course of a compacting process.

According to the invention this problem is solved by a method to determine a slip state of the compactor roller of a soil compactor caused by an oscillation motion of a compactor roller, comprising the steps:
a) Preparation of an acceleration quantity related to the oscillation motion of the compactor roller
b) Based on the acceleration quantity, preparation of an acceleration frequency spectrum,
c) Based on the acceleration frequency spectrum, determining the slip state of the compactor roller.

The present invention makes use of the finding that the frequency portions of the acceleration frequency spectrum contained in a measured or detected acceleration quantity change over time, when a slip occurs between one such compactor roller and the subsoil being compacted. Also the amount of the occurring slip and its different characteristic in the forward and/or backward motion in the course of an oscillation period are reflected in the acceleration-frequency spectrum. Based on the acceleration-frequency spectrum a conclusion can thus be drawn about whether the compactor roller is moving essentially without slip on the subsoil being compacted in the course of a periodic oscillation motion, or whether slip does occur because, for example, a comparatively high degree of compaction was already attained, and to what extent the slip occurs. This information about the presence of slip and about the extent of slip specified according to the invention can be used to adapt the amplitude and/or the frequency of the oscillation motion to reduce the slip that occurs.

In order to be able to make a defined, in particular a quantitative statement about the slip occurring between a compactor roller and a subsoil being compacted, the invention further provides that step c) comprises determination of a slip indicator representing the slip state of the compactor roller.

In one favorable embodiment of the inventive method, the invention provides that at step a) the acceleration quantity is determined based on an acceleration of the compactor roller essentially in a direction parallel to a surface of a subsoil being compacted. The transition into a slip state in the course of the oscillation motion of a compactor roller will generally occur when the circumferential acceleration of the compactor roller exceeds a particular amount. The consequence is that at a comparatively large circumferential acceleration during the transition into a slip state owing to the then reduced advance of the compactor roller, its acceleration essentially parallel to the subsoil being compacted remains approximately constant during the slip phase. The occurrence of slip is reflected in a periodic acceleration quantity in the horizontal direction essentially through regions of approximately constant acceleration, which is accordingly also reflected in the acceleration-frequency spectrum.

For example, the acceleration can be detected or determined essentially parallel to the subsoil being compacted, thus approximately in the horizontal direction, for example, such that the acceleration quantity is determined on the basis of an output signal from at least one acceleration sensor detecting essentially the acceleration of one compactor roller axis of rotation. In this respect it should be pointed out that the compactor roller axis of rotation represents the geometric rotation center of the compactor roller rotating in a compactor frame and thus represents a fictive quantity. The acceleration of this compactor roller axis of rotation similarly corresponds to the acceleration of the entire compactor roller in a direction essentially parallel to the subsoil being compacted.

In step b) the acceleration-frequency spectrum can be determined in a particularly simple manner by Fourier transform, preferably by fast Fourier transform (FFT), of the acceleration quantity.

In a state in which a compactor roller displays essentially no slip with respect to the subsoil being compacted, the sole component or the main component of the acceleration-frequency spectrum will be at a frequency corresponding to the oscillation frequency of the compactor roller. Since in a transition to a slip state it basically can be assumed that a change in amplitude will occur at this oscillation frequency, then according to the invention it is proposed that at step c) the slip state is determined based on a change in amplitude at the oscillation frequency of the compactor roller.

According to one particularly favorable refinement of the method according to the invention, at step c) a slip indicator is determined based on a ratio of the amplitude of the acceleration-frequency spectrum at a first frequency, to the amplitude of the acceleration-frequency spectrum at a second frequency. In particular the invention provides that a frequency of first frequency and second frequency corresponds essentially to the oscillation frequency of the compactor roller. The oscillation frequency in the acceleration-frequency spectrum is that frequency at which the greatest amplitude will occur. In this respect this oscillation frequency of the compactor roller is particularly suitable as a reference for whether or to what extent the base movement of the compactor roller, that is, the periodic back-and-forth rotation motion at the oscillation frequency, is overlapped by other motion states, for example, a slip state, which causes additional frequency fractions in the acceleration-frequency spectrum.

For example, the invention further provides that a frequency of first frequency and second frequency corresponds essentially to an uneven-numbered multiple or to an even-numbered multiple of the oscillation frequency of the compactor roller.

BRIEF DESCRIPTION OF THE DRAWING FIGURES

Figure 2:
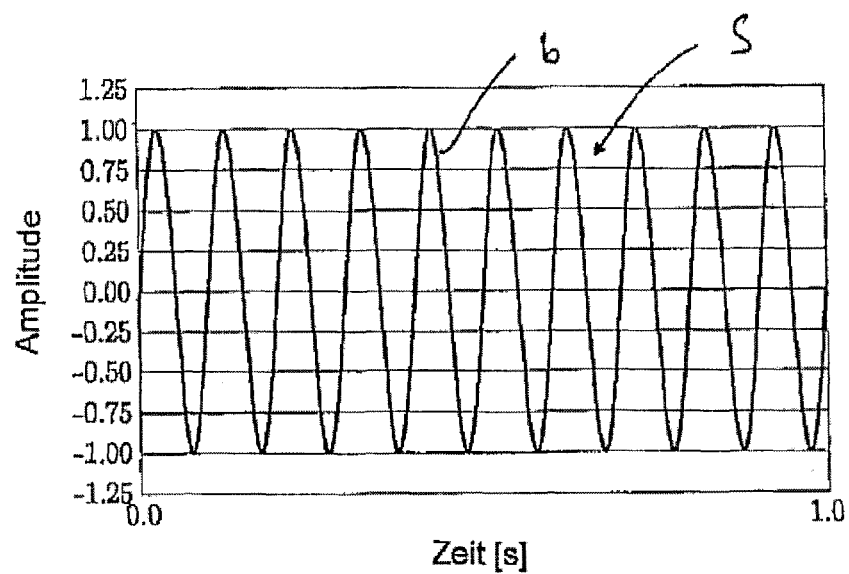
Figure 2:
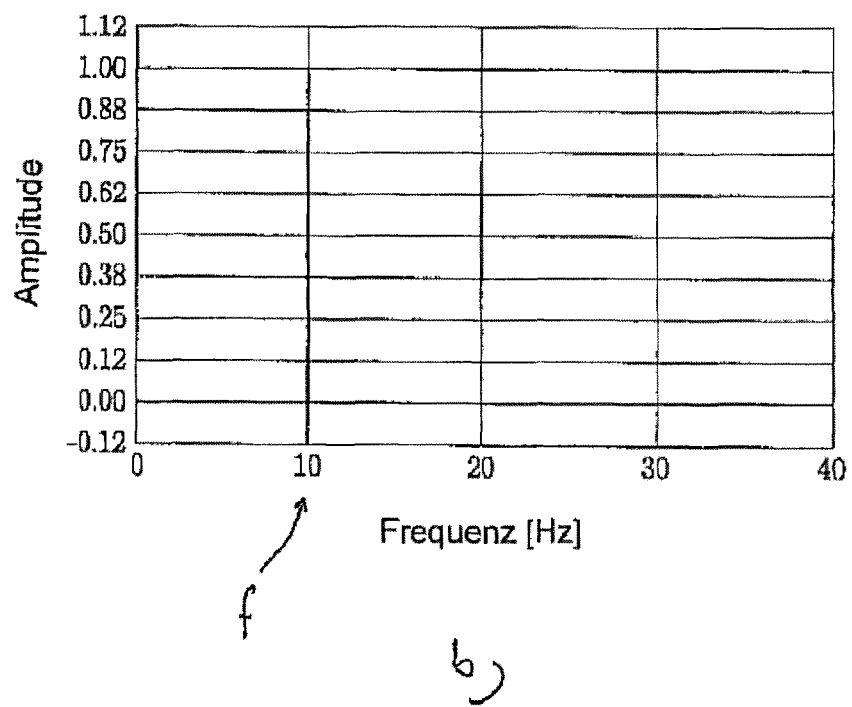
Figure 3:
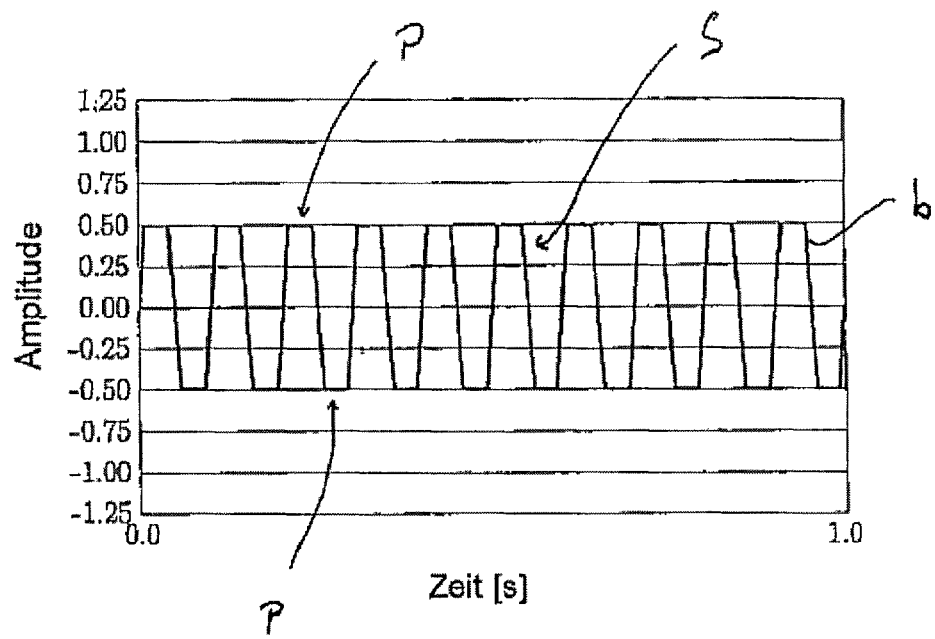
Figure 3:
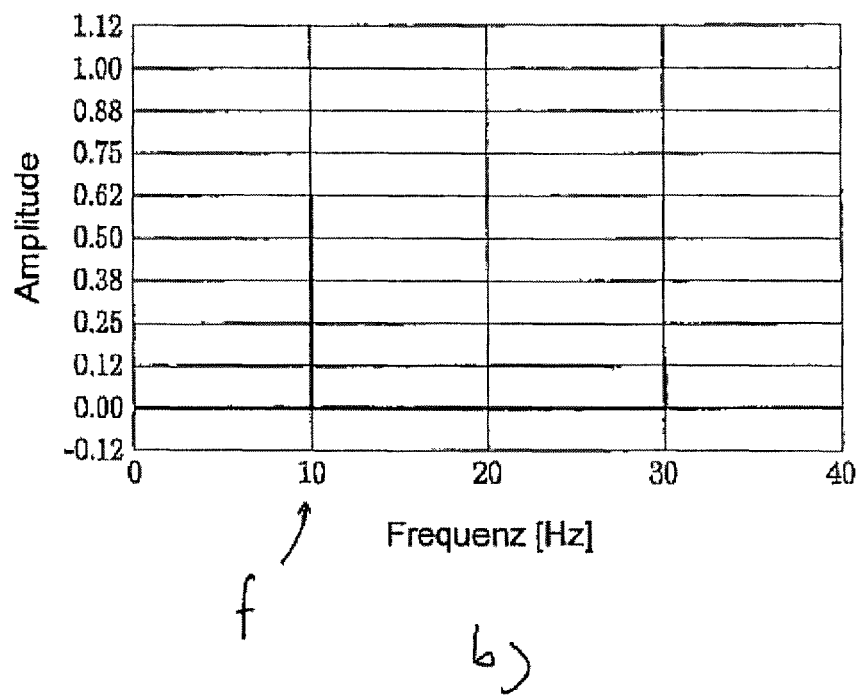

The present invention will be explained in greater detail below with reference to the attached figures. We have:

FIG. 1 A basic depiction of a compactor roller moving along a subsoil being compacted;

FIG. 2 As depicted in a), the horizontal acceleration of the compactor roller of FIG. 1 plotted against time, and as depicted in b), the acceleration-frequency spectrum obtained by Fourier transform of the acceleration;

FIG. 3 As depicted in a), the horizontal acceleration of the compactor roller, plotted against time, with slip occurring symmetrically between the compactor roller and the subsoil being compacted, and as depicted in b), the acceleration-frequency spectrum.

Figure 4:
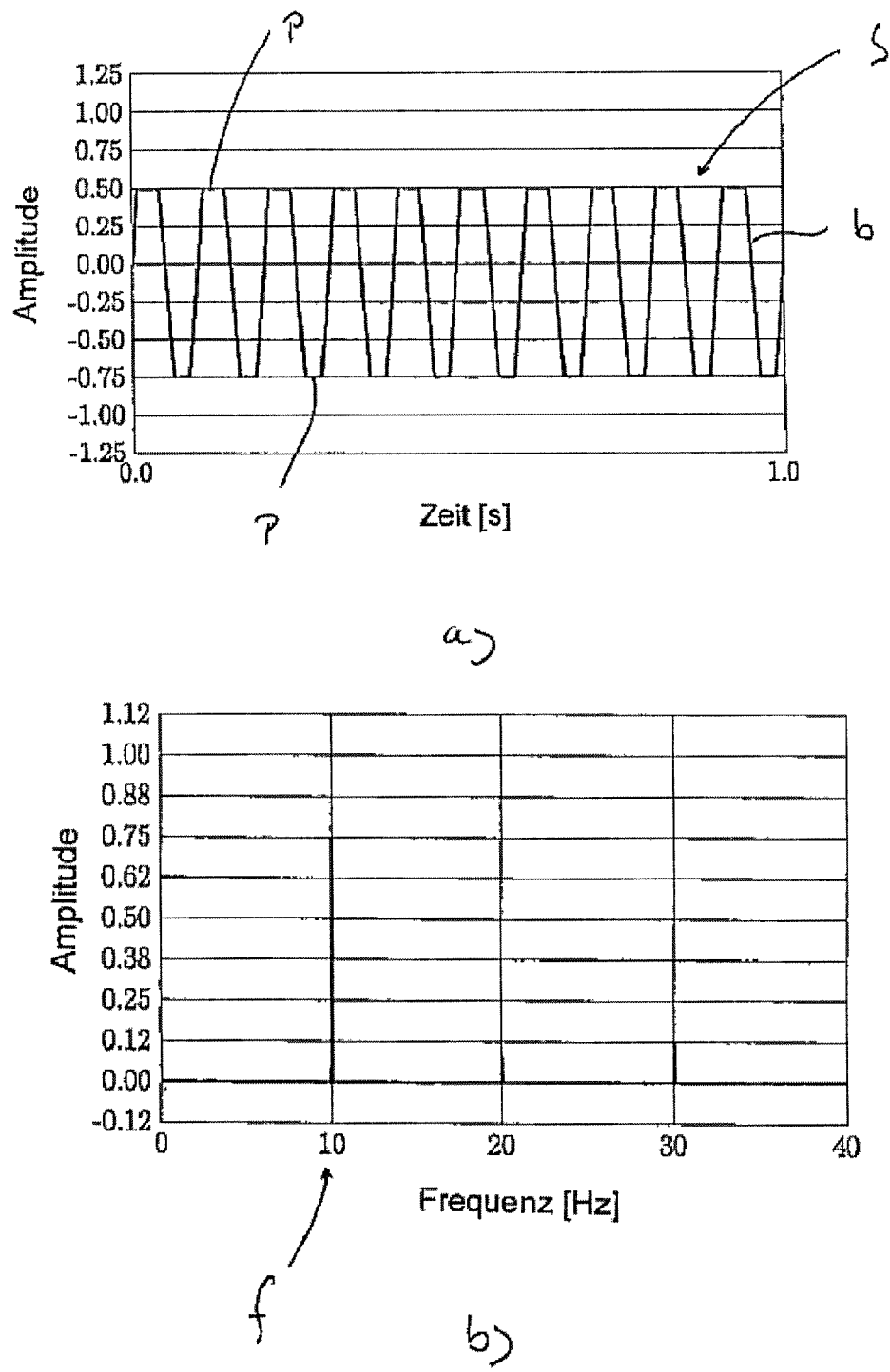
Figure 5:
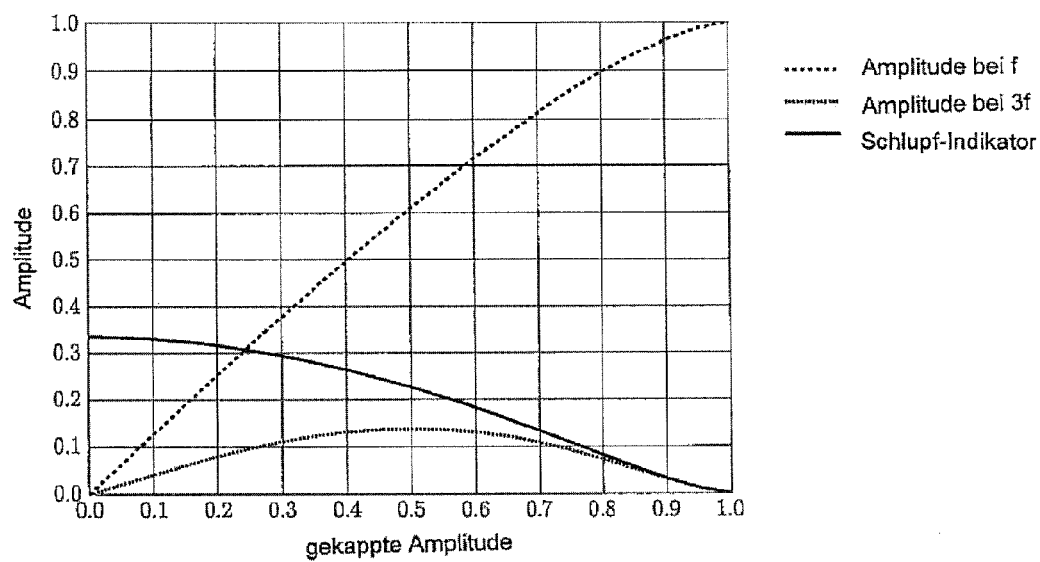

FIG. 4 As depicted in a), the horizontal acceleration of the compactor roller, plotted against time, with slip occurring non-symmetrically between the compactor roller and the subsoil being compacted, and as depicted in b), the acceleration-frequency spectrum;

FIG. 5 The amplitude at oscillation frequency f, the amplitude at three-times the oscillation frequency f, and a slip indicator, all as a function of the magnitude of the amplitude capping caused by the slip.

DETAILED DESCRIPTION OF THE PREFERRED EMBODIMENTS

FIG. 1 shows a schematic representation of a compactor roller 10 of a soil compactor advancing in a travel direction F on a subsoil 12 being compacted. The compactor roller 10 herein can rotate about a compactor roller axis of rotation A supported on a frame of the soil compactor and rotates in a rotation direction R about the compactor roller axis of rotation A during the motion of the soil compactor in travel direction F.

By means of an oscillation mass unit disposed for example in the interior of the compactor roller 10, the compactor roller 10 can be set into a periodic oscillation motion O, which is superimposed on this rotation in the direction of rotation R as periodic motion when the soil compactor is advancing in travel direction F and thereby the compactor roller 10 is rotating in the direction of rotation R about the compactor roller axis of rotation A.

In FIG. 1 it is clear that due to its inherent weight, the compactor roller 10 presses into the subsoil 12 being compacted, and a contact region K is produced. In a region W of the subsoil 12 being compacted, said region preceding the contact region K in travel direction F, a bow wave of the construction material forms on the subsoil 12 being compacted. A corresponding, albeit clearly smaller material pile-up will also form in a region H located to the rear in the travel direction F.

An acceleration sensor unit generally designated by reference number 14 is allocated to the compactor roller 10. This sensor unit can comprise, for example, an acceleration sensor 18 disposed at a roller bushing 16. This acceleration sensor 18 is designed, for example, as a single axis or multiple-axis acceleration sensor and is arranged so that it can determine an acceleration of the compactor roller 10 and/or of the compactor roller axis of rotation A, represented by an arrow B, in a direction essentially parallel to the surface of the subsoil 12 being compacted and also in the travel direction F, and also opposite to the travel direction F, and can output a corresponding sensor signal represented by the curve S in FIG. 1.

If the compactor roller 10 moves across the subsoil 12 being compacted, without oscillation O superimposed on rotation in the direction of rotation R, then due to an absence of change of the motion state of the acceleration sensor 18, no acceleration will be detected. If the oscillation motion O is superimposed on rotation in the direction of rotation R, then the acceleration sensor 18 detects a periodically changing acceleration corresponding to the oscillation frequency of the compactor roller 10. Since in general the compactor roller 10 and/or the bushing 16 supporting it are supported by elastic suspension means on a frame of a soil compactor, the compactor roller 10, due to the oscillation motion O, performs a corresponding periodic motion in the travel direction F and/or opposite the travel direction F with respect to the supporting frame of the soil compactor.

FIG. 2a) shows the signal S, plotted against time, which is output from the acceleration sensor 18, and/or a signal already subjected to filtering in order to remove high-frequency and low-frequency interference. The sensor signal S representing an acceleration quantity b is in the ideal case a periodic signal following a sine function. It displays essentially only frequency portions in the range of the oscillation frequency of the oscillation motion O. In FIG. 2b) this oscillation frequency f is represented at a frequency of 10 Hz as the sole frequency portion of the acceleration-frequency spectrum. It should be pointed out that this acceleration-frequency spectrum can be obtained from the sensor signal S or from the acceleration quantity b, for example by Fourier transform, preferably by fast Fourier transform (FFT). The amplitude at the sole present frequency is presented in FIG. 2b) as normed to a value of 1.00, for instance. Instead of normed values, raw values can also be used.

FIG. 2a) illustrates the case in which the compactor roller 10 is moving with respect to the subsoil 12 being compacted without slip between an outer surface of a roller mantle 20 thereof and the subsoil 12 being compacted. It is emphasized here again that the acceleration quantity b only represents the periodic acceleration of the compactor roller 10, for example, essentially in the horizontal direction caused by the oscillation motion O, that is, in the direction parallel to the surface of the subsoil 12 being compacted, since the uniform and thus non-accelerated rotation in the direction of rotation R in the ideal case causes no acceleration components.

If slippage occurs between the outer surface of the roller mantle 20 and the subsoil 12 being compacted, for example due to increasing degree of compaction, the effective coefficient of static friction between the subsoil 12 being compacted and the roller mantle 20 decreases, then this means that in phases in which the acceleration occurring during the oscillation motion O is a maximum, or exceeds a certain limit value, the compactor roller 10 passes from a state of static friction into a kinetic coefficient of friction state with respect to the subsoil 12 being compacted, that is, it passes into a slip state. In these phases of periodic oscillation motion O denoted by reference letter p in FIG. 3a), the acceleration, which is represented by the acceleration quantity b plotted against time, remains essentially constant. Given a symmetrical slip behavior for the back-and-forth motion of the oscillation motion O, this leads to an essentially symmetrical capping of the periodic profile of the acceleration quantity b around the zero amplitude value with the phases p of approximately constant acceleration.

The acceleration-frequency spectrum shown in FIG. 3b) of this acceleration quantity b occurring or determined in the slip state according to FIG. 3a) also features, in addition to the frequency fraction at 10 Hz corresponding to the oscillation frequency, frequency fractions at uneven multiples of this base frequency, thus of the oscillation frequency f. In FIG. 3b) the frequency portion is evident at three times the oscillation frequency f, thus at 30 Hz. It is also evident that with the appearance of additional frequency portions of this kind, the amplitude at the base frequency, thus of the oscillation frequency f, decreases accordingly.

FIG. 4a) shows a progression of the acceleration quantity b corresponding to FIG. 3a), but for a case of non-symmetrical slip behavior. Non-symmetrical slip behavior of this kind generally occurs when the bow wave discernible in FIG. 1 is present or is clearly pronounced in region W, and in this respect the interaction of the outer surface of the roller mantle 20 with the subsoil 12 being compacted is dependent on the direction of relative motion. This kind of non-symmetrical slip behavior leads to a corresponding non-symmetrical capping of the acceleration quantity b and/or to a corresponding non-symmetrical configuration of phases p, during which in the slip state the acceleration remains approximately unchanged.

The acceleration-frequency spectrum of acceleration quantity b according to FIG. 4a) as represented in FIG. 4b) shows in addition to the portion at the base frequency, that is, the oscillation frequency f, and the frequency portion also present for the case of non-symmetrical slip, at three times the base frequency, thus basically for uneven multiples of the base frequency, and also a frequency portion at two times the base frequency, thus at 20 Hz, and/or basically frequency portions at even-numbered multiples of the base frequency. Here too it is evident that the amplitude at the oscillation frequency f decreases with the appearance of these additional frequency portions, whose amplitude is in general smaller than the amplitude at the base frequency, thus the oscillation frequency f.

This change in the amplitude at the base frequency occurring at the transition of FIG. 2 to FIG. 3 or 4, that is, the change in oscillation frequency f on the one hand, and also the appearance of frequency portions generally not present in the slip-free state, is used by the present invention when slip is present in order make a statement about the presence or the magnitude of slip of the compactor roller 10 with respect to the subsoil 12 being compacted. In particular, according to the invention a slip indicator can be generated based on the amplitudes of frequency portions in the acceleration-frequency spectrum, which can provide information about the presence of slip, the magnitude of the slip or about whether symmetrical or non-symmetrical slip behavior is present. For example, a slip indicator of this kind can be defined as follows:

$$SI = A(f_1)/A(f_2).$$

Thus here the slip indicator SI is defined as the ratio of the amplitudes of various frequency portions $f_1$ and $f_2$ in the acceleration-frequency spectrum. One of these frequency portions, preferably the frequency portion $f_2$, can correspond to the oscillation frequency f, whereas for example the other frequency portion $f_1$, can correspond to an uneven multiple or to an even-numbered multiple of the oscillation frequency f. For example, one could use three times the oscillation frequency as frequency portion $f_1$.

Using this example FIG. 5 shows the progression of amplitude at the oscillation frequency f as a roughly dotted line, and the progression of amplitude for three-times the oscillation frequency f is shown as a finely dotted line, plotted against the extent of capping of the amplitude of the acceleration quantity b. Here the capped amplitude corresponds to 1.0 times the slip-free state in FIG. 2a), whereas the decreasingly capped amplitude represents the state of increasing slip. For the slip-free state, that is, an uncapped amplitude with value 1.0, the amplitude at the oscillation frequency f is a maximum, thus for example at normed value 1.0. With increasing capping, that is, with decreasingly capped amplitude of the acceleration quantity b, the amplitude at frequency f also decreases in the acceleration-frequency spectrum, whereas the amplitude at three times the oscillation frequency, thus at 30 Hz, increases. Accordingly the slip indicator represented by a solid line in FIG. 5 also increases with increasing slip. With increasing slip, thus with increasing capping of the amplitude of the acceleration quantity b, marked changes appear in the acceleration quantity b to the effect that they remain approximately constant only in the ideal case with occurring slip, but in practice a constant progression does not appear, especially with increasing slip. The result is that when the acceleration quantity b drops below the capped amplitude of 0.5, for example, it is still possible to make a determination about the present slip, that is, the slip indicator can still be determined, but it will display a different progression.

The slip-induced appearance of or increase in frequency portions in the acceleration-frequency spectrum can be used, for example by trial and error, to determine a defined relationship between the slip indicator determined in the preceding manner, and the magnitude of the actually occurring slip of a compactor roller, so that not only a qualitative statement can be made about whether slip is present or if an excessive amount of slip is present, but also a quantitative statement can be made about the actually occurring slip.

A statement about the presence of slip can also be made solely based on the observation of amplitude, for example at the oscillation frequency f. This will clearly vary in the transition from the slip-free state, that is, from a static friction state, into a slip state, that is, a kinetic friction state, so that when the change of this amplitude at oscillation frequency f or at any other observed frequency exceeds a particular amount, and/or the rate of change exceeds a certain amount, a conclusion can be drawn about the transition into a slip state.

In an alternative procedure, the acceleration quantity used as the basis for concluding the presence of the slip state can also be taken into account as an acceleration occurring on the roller mantle itself or on a component assembly connected thereon, said acceleration occurring essentially in the circumferential direction or tangential to a radial line with respect to the compactor roller axis of rotation A. Also the roller mantle 20 itself is displaced by the oscillation motion O superimposed on the rotation in the rotation direction R into a periodic back-and-forth motion about the compactor roller axis of rotation A, which leads to a corresponding, periodic acceleration pattern of an acceleration component oriented in the tangential direction or in the circumferential direction. In the slip-free state this acceleration quantity will also follow the periodic acceleration pattern illustrated in FIG. 2a). During the transition into a slip state, that is, into a kinetic friction state, this acceleration quantity will not remain generally constant, but rather owing to the loss of a significant portion of a reaction force, will have a definite rise, for example, a nearly jump-like profile which differs significantly from the sine-like progression. This transition also forms in the acceleration-frequency spectrum because in addition to the frequency portion at the oscillation frequency f, additional frequency portions appear and the amplitude at oscillation frequency f will decrease. Likewise as described above, a slip indicator can thus be determined from the ratio of amplitudes at different frequency portions, for example, or the transition between a static friction state and a kinetic friction state can be recognized by observation of the change in amplitude, for example at the oscillation frequency f.

In conclusion it should be pointed out again that the progression of the acceleration quantity described above with reference to FIGS. 2 to 4, and the resulting acceleration-frequency spectrum each represents an idealized case, in which on the one hand the oscillation motion follows a periodic function defined by a single oscillation frequency and upon the appearance of slip, the acceleration remains essentially constant until the static friction state is re-established. But in reality, the profile of oscillation motion of the oscillation frequency will contain other frequency portions, although with smaller amplitude in the acceleration-frequency spectrum, and upon the appearance of slip, frequency portions will appear at frequencies other than the even-numbered or uneven-numbered multiples of the oscillation frequency. However, this does not restrict the possibility of taking into account specifically defined frequency portions with their particular amplitudes in the determination of the slip indicator, in particular to use the base frequency, that is, the oscillation frequency f, and the even-numbered or uneven-numbered multiples thereof.

The invention claimed is:

1. Method to determine a slip state of the compactor roller of a soil compactor caused by an oscillation motion of a compactor roller, comprising the steps:
   a) preparing an acceleration quantity related to the oscillation motion of the compactor roller based on an acceleration of the compactor roller essentially in a direction parallel to a surface of a soil being compacted;
   b) based on the acceleration quantity, preparing an acceleration frequency spectrum; and
   c) based on the acceleration frequency spectrum, determining the slip state of the compactor roller by determining a slip indicator representing the slip state of the compactor roller, wherein said slip indicator is determined based on a ratio of the amplitude of the acceleration-frequency spectrum at a first frequency to the amplitude of the acceleration-frequency spectrum at a second frequency.

2. Method according to claim 1, wherein the acceleration quantity is determined on the basis of an output signal from at least one acceleration sensor detecting essentially the acceleration of one compactor roller axis of rotation.

3. Method according to claim 1 wherein at step b) the acceleration-frequency spectrum determined by Fourier transform of the acceleration quantity.

4. Method according to claim 3, wherein the Fourier transform is a fast Fourier transform.

5. Method according to claim 1 wherein at step c) the slip state is determined based on a change in amplitude at the oscillation frequency of the compactor roller.

6. Method according to claim 1, wherein a frequency of the first frequency and second frequency corresponds essentially to illation frequency of the compactor roller.

7. Method according to claim 1, wherein a frequency of first frequency and second frequency corresponds essentially to an uneven-numbered multiple or to an even-numbered multiple of the oscillation frequency of the compactor roller.

* * * * *